United States Patent
Ouwerkerk et al.

(10) Patent No.: US 10,085,695 B2
(45) Date of Patent: Oct. 2, 2018

(54) MENTAL BALANCE OR IMBALANCE ESTIMATION SYSTEM AND METHOD

(71) Applicant: KONINKLIJKE PHILIPS N.V., Eindhoven (NL)

(72) Inventors: Martin Ouwerkerk, Culemborg (NL); Joanne Henriette Desiree Monique Westerink, Eindhoven (NL); Tatiana Aleksandrovna Lashina, Eindhoven (NL); Leszek Holenderski, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1064 days.

(21) Appl. No.: 14/356,691

(22) PCT Filed: Nov. 12, 2012

(86) PCT No.: PCT/IB2012/056354
§ 371 (c)(1),
(2) Date: May 7, 2014

(87) PCT Pub. No.: WO2013/076615
PCT Pub. Date: May 30, 2013

(65) Prior Publication Data
US 2014/0288401 A1   Sep. 25, 2014

Related U.S. Application Data

(60) Provisional application No. 61/562,627, filed on Nov. 22, 2011.

(51) Int. Cl.
*A61B 5/00*    (2006.01)
*A61B 5/053*   (2006.01)
(Continued)

(52) U.S. Cl.
CPC .......... *A61B 5/7278* (2013.01); *A61B 5/0531* (2013.01); *A61B 5/0533* (2013.01);
(Continued)

(58) Field of Classification Search
None
See application file for complete search history.

(56) References Cited

U.S. PATENT DOCUMENTS 6,233,471 B1 *   5/2001   Berner ............... A61B 5/14532
                                                        600/309
7,052,472 B1 *   5/2006   Miller ..................... A61B 5/01
                                                        600/549
(Continued)

FOREIGN PATENT DOCUMENTS

EP   1407713 A1     4/2004
EP   2196138 A2 *  6/2010  ........... A61B 5/0205
(Continued)

OTHER PUBLICATIONS

Westerink et al, "Emotion Measurement Platform for Daily Life Situations", Affective Computing and Intelligent Interaction and Workshops, Sep. 10, 2009, p. 1-6.
(Continued)

*Primary Examiner* — Matthew Kremer

(57) ABSTRACT

The present invention relates to a mental balance or imbalance estimation system (100) and method for estimating a level of mental balance or imbalance of a user (1). The system comprises a skin conductance sensor (20) for sensing the skin conductance of the user (1), the skin conductance over time forming a skin conductance trace (22). The system further comprises a processing unit (10) for receiving and processing the skin conductance trace (22), the processing unit configured to determine at least one stimulus response (24) in the skin conductance trace (22), to determine an estimated cortisol level trace (28) of the user (1) based on the
(Continued)

determined at least one stimulus response (24), and to determine the estimated level of mental balance or imbalance of the user (1) based on the estimated cortisol level trace (28).

9 Claims, 11 Drawing Sheets

(51) Int. Cl.
 *A61B 5/16* (2006.01)
 *A61B 5/145* (2006.01)
 *A61B 5/1477* (2006.01)

(52) U.S. Cl.
 CPC ........ *A61B 5/1477* (2013.01); *A61B 5/14546* (2013.01); *A61B 5/165* (2013.01); *A61B 5/681* (2013.01); *A61B 5/7225* (2013.01); *A61B 5/7275* (2013.01); *F04C 2270/0421* (2013.01)

(56) References Cited

U.S. PATENT DOCUMENTS

| | | | |
|---|---|---|---|
| 7,921,066 B2 | 4/2011 | Van Dyke Parunak et al. | |
| 2003/0139654 A1* | 7/2003 | Kim | A61B 5/02405 600/300 |
| 2004/0039254 A1* | 2/2004 | Stivoric | A61B 5/0205 600/300 |
| 2008/0081963 A1 | 4/2008 | Naghavi et al. | |
| 2009/0264711 A1 | 10/2009 | Schuler et al. | |
| 2010/0022852 A1* | 1/2010 | Westerink | A61B 5/0533 600/301 |
| 2011/0152635 A1 | 6/2011 | Morris et al. | |
| 2012/0271121 A1* | 10/2012 | Della Torre | A61B 5/024 600/301 |

FOREIGN PATENT DOCUMENTS

| | | |
|---|---|---|
| JP | 2005305132 A | 11/2005 |
| WO | 2006090371 A2 | 8/2006 |
| WO | 2008099320 A1 | 8/2008 |

OTHER PUBLICATIONS

Kirschbaum et al, "Consistent Sex Differences in Cortisol Responses to Psychological Stress", Psychosomatic Medicine, vol. 54, No. 6, Jan. 1, 1992, p. 648-657.

Mc Ewen, "Central Effects of Stress Hormones in Health and Disease: Understanding the Protective and Damaging Effects of Stress and Stress Mediators", European Journal of Pharmacology 583, 2008, p. 174-185.

Sterling et al, "Allostasis: A New Paradigm to Explain Arousal Pathology", Handbook of Life Stress, Cognition and Health, John Wiley and Sons, 1988, p. 629-649.

McEwen, "Protective and Damaging Effects of Stress Mediators", Seminars in Medicine of the Beth Israel Deaconess Medical Center, vol. 338, No. 3, p. 171-179.

* cited by examiner

MENTAL BALANCE OR IMBALANCE ESTIMATION SYSTEM AND METHOD

CROSS-REFERENCE TO PRIOR APPLICATIONS

This application is the U.S. National Phase application under 35 U.S.C. § 371 of International Application No. PCT/IB2012/056354, filed on Nov. 12, 2012, which claims the benefit of U.S. Provisional Application No. 61/562,627, filed on Nov. 22, 2011. These applications are hereby incorporated by reference herein.

FIELD OF THE INVENTION

The present invention relates to a mental balance or imbalance estimation system and method for estimating a level of mental balance or imbalance of a user. The present invention further relates to a wearable device wearable by a user and comprising such mental balance or imbalance estimation system, as well as to a corresponding processing unit and a computer program implementing such method.

BACKGROUND OF THE INVENTION

The term allo stasis has been introduced in the chapter "Allostasis: A new paradigm to explain arousal pathology, In Fisher, S., Reason, J. (Eds.) Handbook of Life Stress, Cognition and Health, John Wiley and Sons, New York, (1988), p 629-649". Hemostatis emphasizes that the body's internal environment is held constant by the self-correcting (negative feedback) actions of its constituent organs. Allostasis emphasizes that internal milieu varies to meet perceived and anticipated demand. In other words, allostasis refers to the active process by which the body responds to daily events and maintains homeostasis.

In the paper "Central effects of stress hormones in health and disease: Understanding the protective and damaging effects of stress and stress mediators, B. S. McEwen, European Journal of Pharmacology 583 (2008), p 174-185" the central effects of stress hormones in health and disease are described. Stress begins in the brain and affects the brain, as well as the rest of the body. Acute stress responses promote adaptation and survival via responses of neural, cardiovascular, autonomic, immune and metabolic systems. Chronic stress can promote and exacerbate pathophysiology through the same systems that are dysregulated. The burden of chronic stress and accompanying changes in personal behaviors (smoking, eating too much, drinking, poor quality sleep; otherwise referred to as "lifestyle") is called allostatic overload. It is clear that chronic stress is not healthy.

Quantification of stress is for example described in WO 2006/090371 A2. WO 2006/090371 A2 discloses a system and method for monitoring one or more physiological parameters of a user. The system comprises one or more wearable sensor modules sensing the one or more physiological parameters. One or more transmitters wirelessly transmit signals indicative of values of the one or more physiological parameters to a mobile monitor. The mobile monitor comprises a first processor processing the signals received from the transmitter in real time using expert knowledge. A device provides one or more indications of results of the processing. In an embodiment the first processor is configured to calculate from the first signals one or both of the parameter indicated of an arousal state of the user and a parameter indicative of an emotional state of the user. Further, the calculation of the parameter indicative of an arousal state of the user can include calculating a score of a sympathetic or parasympathetic activity of the user using an algorithm based on anyone or more of the user's electrodermal activity, heart rate, EDA variability, and HR variability.

It is currently becoming more and more important to not only quantify stress, but to actually balance stress (e.g. due to a more demanding lifestyle or faster pace of life). US 2009/0264711 A1 discloses a method and apparatus for behavior modification. During operation an apparatus learns what context causes desired and undesired physiological parameters and then coaches a user to be aware of context causing undesired behavior and avoid future occurrences. The apparatus may then recommend behavior modification prior to the parameter reaching elevated status. Because an individual will be warned when situations exist that will cause undesired physiological parameters, the apparatus will suggest to the user a method to alleviate the situation, for example, substituting an activity or context that creates desired physiological patterns. The user will then be able to take appropriate steps to alleviate the situation.

However, a system with a real-time assessment of the cumulative stress load in terms of the deviation from allo stasis, and the danger of allo static overload, is presently not available. Therefore, there is a need to provide an improved system for estimating the mental balance of a user.

SUMMARY OF THE INVENTION

It is an object of the present invention to provide an improved mental balance or imbalance estimation system and method, as well as a wearable device comprising such system, a corresponding processing unit and a computer program implementing such method.

In a first aspect of the present invention a mental balance or imbalance estimation system for estimating a level of mental balance or imbalance of a user is presented, the system comprising a skin conductance sensor for sensing the skin conductance of the user, the skin conductance over time forming a skin conductance trace. The system further comprises a processing unit for receiving and processing the skin conductance trace, the processing unit configured to determine at least one stimulus response in the skin conductance trace, to determine an estimated cortisol level trace of the user based on the at least one stimulus response, and to determine the estimated level of mental balance or imbalance of the user based on the estimated cortisol level trace.

In a further aspect of the present invention a wearable device is presented wearable by a user, the device comprising the mental balance or imbalance estimation system according to the invention.

In a further aspect of the present invention a processing unit is presented for receiving and processing a skin conductance trace, the processing unit configured to determine at least one stimulus response in the skin conductance trace, to estimate a cortisol level trace based on the at least one stimulus response, and to estimate a level of mental balance or imbalance of a user based on the estimated cortisol level trace.

In a further aspect of the present invention a mental balance or imbalance estimation method is presented for estimating a level of mental balance or imbalance of a user, the method comprising: receiving a skin conductance trace, determining at least one stimulus response in the skin conductance trace, estimating a cortisol level trace of the user based on the at least one stimulus response, and estimating the level of mental balance or imbalance of the user based on the estimated cortisol level trace.

The basic idea of the invention is to estimate or model a (salivary) cortisol level trace (which is a cortisol level over time) based on skin conductance measurements. It is known that a stimulus (or stressor or emotional event) causes (with a short latency) a stimulus response in the skin conductance (or skin conductance response) which can be measured. The inventors have found that there is a specific relationship between a stimulus response (or skin conductance response) in the skin conductance trace and a (salivary) cortisol time response of a user. Thus, there is a specific correlation between the measured skin conductance response (or stimulus response) and a subsequent cortisol response. The cortisol response linked to a stimulus response has in particular a specific (time) latency. This latency is in particular much bigger than the latency between the stimulus and its stimulus response. In particular, it has been found that there is a specific latency between the peak in the skin conductance trace and the peak of the corresponding cortisol time response. Also, the inventors have found that that the cortisol time responses can be cumulated or added on top of each other.

Using this knowledge, the level of mental balance or imbalance of a user can be estimated. It shall be understood that a level of mental balance and a level of mental imbalance can be used interchangeably. Mental balance is the opposite of mental imbalance, and vice versa. A high level of mental balance corresponds to a low level of mental imbalance, and a low level of mental balance corresponds to a high level of mental imbalance.

In particular, a quantification of the cumulative effect of subsequent stimuli (or stressors) in a specific time frame (e.g. a time frame of several hours) can be provided. With the present invention not only the allostatic load can be assessed, but even a prediction of an altered stress response in the near future can be given after the occurrence of severe stimuli (or stressors). Allostatic load is similar to cumulative stimulus response severity (or balance/imbalance state), but the time lag is absent.

The system or method estimates or derives a measure for mental balance (or imbalance) derived from skin conductance measurements (for example using a wearable device). This measure or level of mental balance (or imbalance) can not only give an indication of the momentary state of mental balance (or imbalance) of the user (e.g. person), but it can also make an estimation of the upcoming levels of mental balance (or imbalance). For example, the user can be warned about a potential mental imbalance period during a following time period (e.g. during the next 60 minutes). In particular, the estimation or prediction of the level of imbalance in the case of a severe emotional event can extend a specific time period into the future (e.g. 150 minutes into the future). As such, the system or method can guide a user (e.g. person) to prevent overstressed states that can be harmful to the health of the user. Based on the estimated imbalance level, an output can be rendered to the user, for example in the form of an advice not to drive a car for such time period into the future. Moreover, the system or method could use the forecast of upcoming mental imbalance in relation to other known upcoming events (e.g. from an agenda) in order to predict situations that are potentially harmful to the health of the user.

Preferred embodiments of the invention are defined in the dependent claims. It shall be understood that the claimed method, wearable device or processing unit has similar and/or identical preferred embodiments as the claimed system and as defined in the dependent claims.

In a first embodiment the system further comprises a memory for storing the estimated cortisol level trace which is determined by cumulating multiple estimated cortisol time responses, wherein each estimated cortisol time response is based on one stimulus response. Thus, the cortisol time responses are added on top of each other. In particular, for each point of time, the cortisol levels of different cortisol time responses for that point of time can be added. In this way a quantification of the cumulative effect of subsequent stimuli (or stressors) in a specific time frame (e.g. a time frame of several hours) can be provided. Based on these cumulated cortisol responses the level of mental balance (or imbalance) can be estimated.

In a variant of this embodiment the processing unit is configured to estimate each cortisol time response as $$\text{Cortisol}(t) = g * \frac{\exp\left(-\frac{t}{c_d}\right)}{1 + \frac{c_r^2}{t^2}},$$

where $g$ is a gain, $c_r$ is a rise coefficient and $c_d$ is a decay coefficient. In this way an estimation of the cortisol response which closely resembles a salivary cortisol response of the user in reality can be provided.

In another variant the estimated cortisol time response depends on an input information indicating the sex of the user which is input into the system. By taking the sex of the user into account a more accurate estimation of the level of mental balance (or imbalance) can be given.

In another variant the processing unit is configured to determine one of the at least one stimulus response at a specific start point of time, and the corresponding estimated cortisol time response has its start point at the specific start point of time and lasts to its end point at a predefined end time in the future. In this way an estimation or prediction of an upcoming level of mental balance (or imbalance) in the future by calculating and/or evaluating the cortisol level trace for a future time period of the length of the predefined end time can be provided, or an estimation of the momentary state of mental balance (or imbalance) of the user can be provided by calculating and/or evaluating the cortisol level trace for a past time period of the length of the predefined end time.

In a variant the corresponding estimated cortisol time response rises to its peak point, which is at a predefined peak point of time, with a predefined rise coefficient and falls to its end point, which is at the predefined end time, with a predefined decay coefficient. In this way an estimation of the cortisol response which closely resembles a salivary cortisol response of the user in reality can be provided. Just as an example, the rise coefficient can be between 27 and 29, in particular 28, the decay coefficient can be between 22 and 24, in particular 23, for a male, the decay coefficient can be between 14 and 16, in particular 15, for a female, the gain can be between 154 and 156, in particular 155, for a male and/or the gain can be between 269 and 271, in particular 270, for a female.

In a variant the predefined peak point of time is about 30 minutes after the specific start point of time. This latency in time between the peak in the skin conductance trace and the peak of the corresponding cortisol time response has shown to closely resemble reality.

In another variant the predefined end point of time is about 90 minutes after the specific start point of time if an input information indicates a female as the user, and/or wherein the predefined end point of time is about 150 minutes after the specific start point of time if the input information indicates a male as the user. These end times for both males and females have shown to closely resemble reality.

In a further embodiment the processing unit is configured to determine the at least one stimulus response in the skin conductance trace by determining peaks in the first order derivative of the skin conductance. This is an easy way of determining a stimulus response (or stressor) in a skin conductance signal.

In a variant the height of the peak point of the cortisol time response is proportional to the height of the peak in the first derivative of the skin conductance trace. Thus, the cortisol level, and thus the level of mental balance (or contribution to allostatic load), is quantified by the height of the peak in the first derivative of the skin conductance trace or signal.

In another embodiment the processing unit is configured to determine, based on the estimated cortisol level trace, at least three (or more) different states that depict various levels of mental balance (or imbalance). In this way a valuable feedback or output can be provided to the user. The at least three states can for example be a "safe balanced" state, a "call for attention" state, and a "take action" (e.g. a "green" state, a "yellow" state, and a "red" state).

In another embodiment the processing unit is configured to determine the estimated level of mental balance or imbalance for the current point of time. In this way an estimation of the momentary state of mental balance (or imbalance) of the user can be provided, in particular by evaluating the cortisol level trace of a past time period.

In another embodiment the processing unit is configured to determine the estimated level of mental balance or imbalance for a future point of time or future period of time. In this way an estimation or prediction of an upcoming level of mental balance (or imbalance) in the future can be provided, in particular by evaluating the cortisol level trace considering for a future time period.

In another embodiment the system comprises an output unit for outputting the level of mental balance or imbalance to the user. In this way the user can be informed about his current and/or predicted level of mental balance (or imbalance). The user may then act accordingly.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

The role of the hormone cortisol for stress has been investigated in the past. For example, in the paper "Consistent Sex Differences in Cortisol Responses to Psychological Stress, Clemens Kirschbaum, Phd, Stefan Wust, and Dirk Hellhammer, Phd, Psychosomatic Medicine 54 (1992), p 648-657", which is incorporated by reference herein, the endocrinological effects of psychological stress are described.

The hypothalamus-pituitary-adrenal axis (HPA) serves vital physiological functions in the mammalian organism both under unstimulated conditions as well as during challenges such as physical and emotional stress, such as described in "Studies on adaptation, Selye H., Endocrinology 21 (1937) p 169-188", which is incorporated by reference herein. Besides impact on structures in the central nervous system mediated by corticotrophin-releasing hormone (CRH), most peripheral and central effects of HPA activity are modulated by the major glucocorticoid hormone cortisol (in man) or corticosterone (in rodents), respectively. The presence of moderate cortisol levels throughout the day is mandatory for basic physiological processes like cardio-vascular functions. On the other hand, vigorous glucocorticoid responses have been shown to counterbalance or prevent negative effects brought about by stressors, such as described in "Physiological functions of glucocorticoids in stress and their relation to pharmacological actions, Munck A, Guyre P M, Holbrook N.J., Endocr Rev 5 (1984) p 25-44", which is incorporated by reference herein.

In the paper by Kirschbaum et al. mentioned above the adrenocortical responses of healthy adolescents and adults to a psychosocial stress protocol in a laboratory setting are described. By means of repeated cortisol measures in saliva the time evolution of this response has been determined for both males and females.

Figure 1:
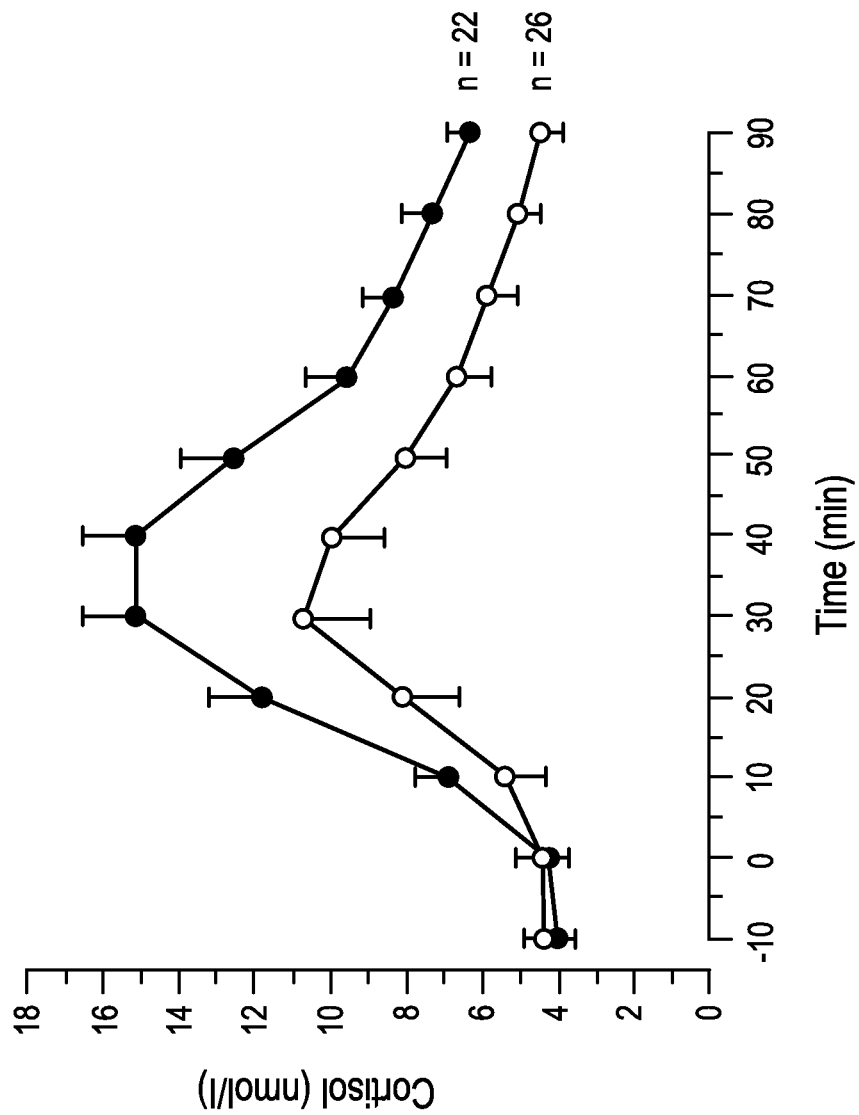
FIG. 1 shows an exemplary cortisol time response.

FIG. 1 shows an exemplary cortisol time response. FIG. 1 shows the cortisol time response caused by a stress response for males (closed circles) and females (open circles), as disclosed in the paper by Kirschbaum et al. mentioned above. The cortisol time response is the trace of the cortisol level (absolute value measured in nmol/l in FIG. 1) over time. Even though FIG. 1 is a result disclosed in the paper by Kirschbaum et al. mentioned above, it stands for a general cortisol time response. This general cortisol time response is relevant for the present invention.

The inventors have found that there is a specific relationship between a stimulus response (or skin conductance response) in the skin conductance trace and a (salivary) cortisol time response of a user. Thus, there is a specific correlation between the measured skin conductance response (or stimulus response) and a subsequent cortisol time response. The cortisol response linked to a stimulus response has in particular a specific (time) latency. This latency is in particular much bigger than the latency between the stimulus and its stimulus response. Also, the inventors have found that that the cortisol time responses can be cumulated or added on top of each other. Using this knowledge, the level of mental balance or imbalance of a user can be estimated.

Figure 2:
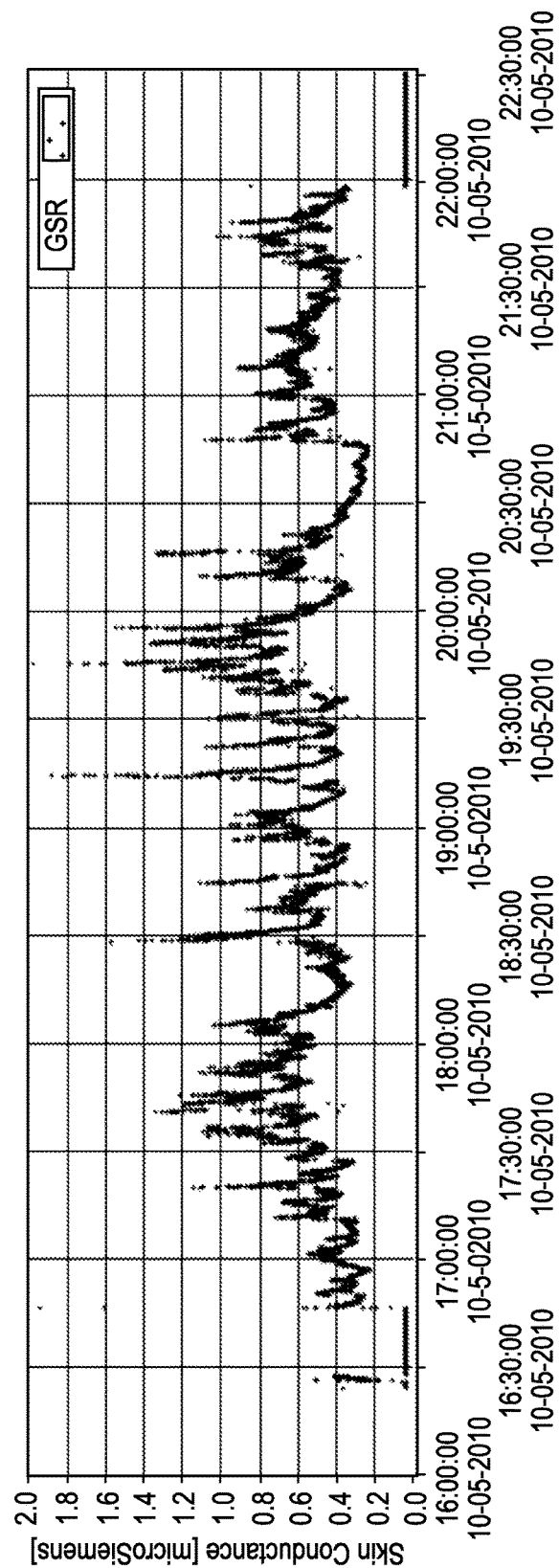
FIG. 2 shows an exemplary skin conductance trace measured by a skin conductance sensor.

FIG. 2 shows an exemplary skin conductance trace measured by a skin conductance sensor. The sensor can for example be integrated in or measured with the wearable device disclosed herein. The x-axis in FIG. 2 denotes the time t over a period of several hours, here from about 16 o'clock (4 p.m.) to 22.30 o'clock (10.30 p.m.). Thus, a skin conductance trace is formed over several hours. In FIG. 2, the y-axis denotes the measured skin conductance values, also called galvanic skin response (GSR) or electrodermal activity (EDA), measured in µS. Each point of the skin conductance trace indicates the skin conductance value sensed by the skin conductance sensor at that specific point in time t. Skin conductance (or GSR or EDA), is a measure of the electrical conductance of the skin, which varies with its moisture level, thus the sweat gland activity. Emotional events or stimuli show as peaks with a steeper rising slope and a gentler down slope. In FIG. 2, each peak corresponds to a response of the sympathetic nervous system to an emotionally arousing event (communicated via the vagal nerve to the sweat glands of the skin). This peak is also called skin conductance response (or stimulus response). Emotionally arousing events or stimuli can be viewed as psychological stress, in contrast to physical exercise, which can be viewed as physical stress. Thus, an emotional event or stimulus causes (with a short latency) a stimulus response in the skin conductance (or skin conductance response) which can be measured.

Figure 3:
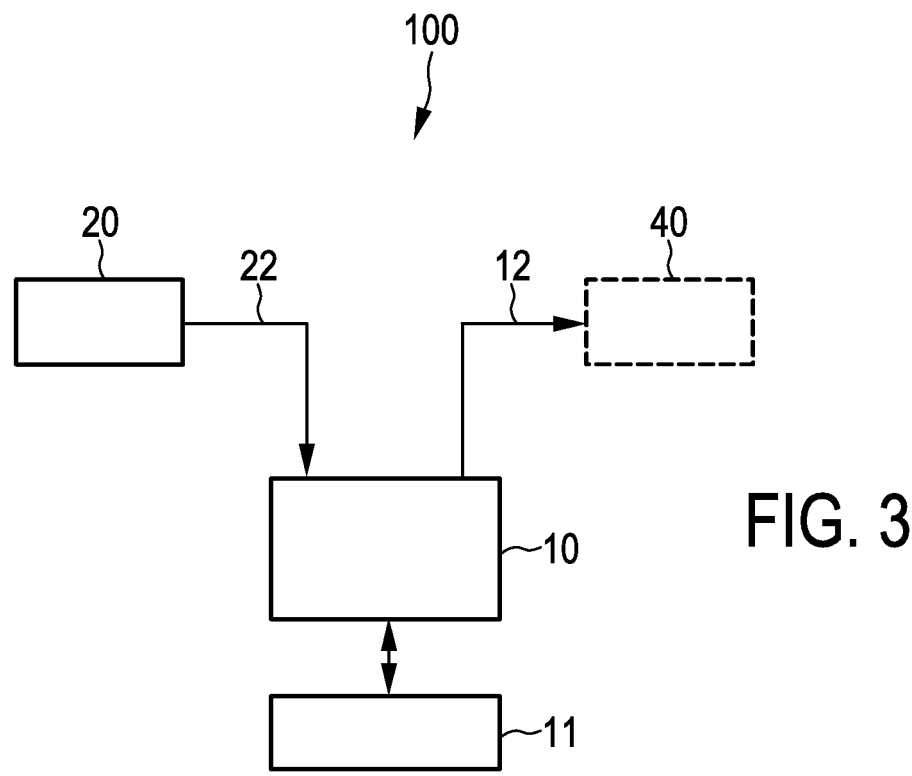
FIG. 3 shows a mental balance or imbalance estimation system according to an embodiment.

FIG. 3 shows a mental balance or imbalance estimation system 100 according to an embodiment. The mental balance or imbalance estimation (or determination) system for estimating (or determining) a level 12 of mental balance or imbalance of a user comprises a skin conductance sensor 20 for sensing the skin conductance of the user. The skin conductance measured by the sensor 20 over time forms a skin conductance trace 22. The system further comprises a processing unit 10 (or mental balance/imbalance level estimation unit or mental balance/imbalance level estimator) for receiving and processing the skin conductance trace 22. The processing unit 10 can be any type of suitable processing unit or processor, such as for example a microprocessor/microcontroller, or embedded microcontroller, but not limited thereto. It will be understood that the skin conductance sensor 20 and the processing unit 10 can be part of the same device (e.g. wearable device or wristband) or can be in two separate devices.

The processing unit 10 is configured to determine at least one stimulus response in the skin conductance trace 22 (e.g. by determining the first order derivative of the skin conductance), to estimate a cortisol level trace of the user based on the determined at least one stimulus response, and to determine (or compute) the estimated level 12 of mental balance/imbalance of the user based on the estimated cortisol level trace. Optionally, as indicated by the dashed lines in FIG. 3, the system can comprise an output unit 40 for outputting or rendering the level 12 of mental balance or imbalance to the user. It will be understood that the output unit 40 and the processing unit 10 can be part of the same device (e.g. wearable device or wristband) or can be in two separate devices.

The system can further comprise a memory 11 for storing the estimated cortisol level trace 28. The processing unit 10 can store the cortisol level trace 28 into the memory 11 and/or can read the stored trace from the memory 11. The processing unit 28 is configured to determine (or compute) an estimated cortisol time response 26 for each determined stimulus response 24. The estimated cortisol time response 26 is then added to the cortisol level or cortisol level trace 28 in the memory. Thus, multiple estimated cortisol time responses 26 are cumulated in order to estimate the cortisol level trace 28 which is stored in the memory 11. More specifically, for each point of time, the cortisol levels of different cortisol time responses for that point of time are added or cumulated. The memory can be any suitable memory, such as for example a memory register or RAM (random access memory). It will be understood that the memory 11 and the processing unit 10 can be part of the same device (e.g. wearable device or wristband) or can be in two separate devices.

Figure 4:
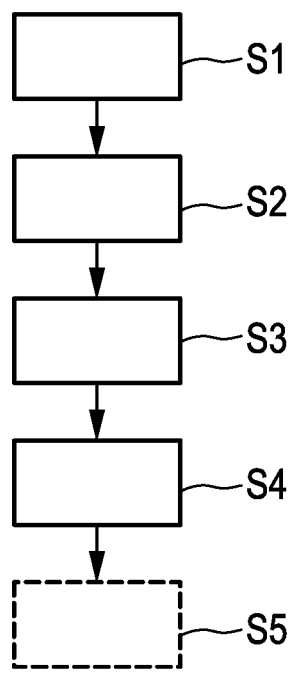
FIG. 4 shows a mental balance or imbalance estimation method according to an embodiment.

FIG. 4 shows a mental balance or imbalance estimation method according to an embodiment. The method for estimating a level of mental balance or imbalance of a user comprises the step S1 of receiving a skin conductance trace, the step S2 of determining at least one stimulus response in the skin conductance trace (e.g. by determining the first order derivative of the skin conductance), the step S3 of estimating a cortisol level trace of the user based on the determined at least one stimulus response, and the step S4 of determining the estimated level of mental balance or imbalance of the user based on the estimated cortisol level trace. These steps can also be performed by a processing unit or a computer program comprising program code means for causing a computer to carry out these steps. Optionally, as indicated by the dashed lines, the method can further comprise a step S5 of outputting the level of mental balance or imbalance to the user.

In one example, the estimated level of mental balance (or imbalance) is determined for the current (or momentary) point of time by calculating and/or evaluating the cortisol level trace of a past time period (e.g. 90 minutes into the past for females and 150 minutes into the past for males). For example, the processing unit 10 can read the cortisol level trace 28 for the past period (e.g. past 90 minutes) from the memory 11 in order to determine the level of mental balance for the current point of time. In another example, the estimated level of mental balance (or imbalance) is determined or predicted for a future point of time (or future period of time) by calculating and/or evaluating the cortisol level trace for a future time period (e.g. 90 minutes into the future for females and 150 minutes into the future for males). For example, the processing unit 10 can read the cortisol level trace 28 for the future period (e.g. future 90 minutes) from the memory 11 in order to determine the level of mental balance for the future point of time.

Figure 5:
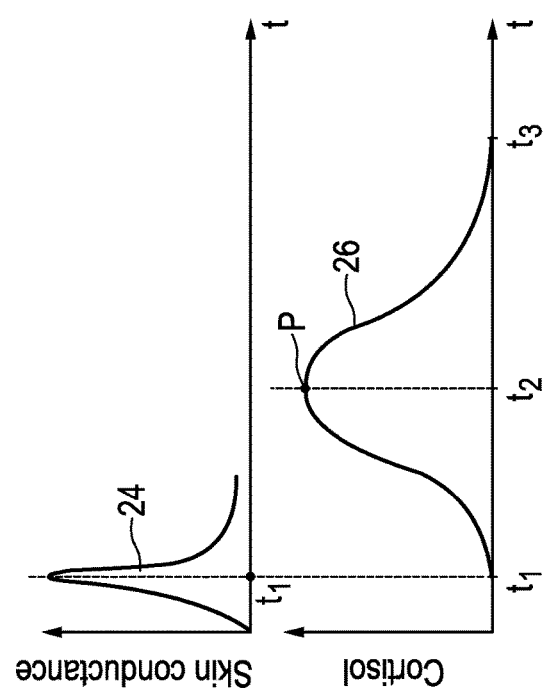
FIG. 5 shows an exemplary stimulus response and a corresponding cortisol time response.

FIG. 5 shows an exemplary stimulus response 24 (or skin conductance response) of a skin conductance trace 22 (top diagram of FIG. 5) and a corresponding cortisol time response 26 (bottom diagram of FIG. 5). As can be seen in FIG. 5, the stimulus response 24 is determined at a specific start point of time t1, and the corresponding estimated cortisol time response 26 has its start point at the specific start point of time t1 and lasts to its end point at a predefined end time t3 in the future. More specifically, the cortisol time response 26 rises to its peak point P, which is at a predefined peak point of time t2, with a predefined rise coefficient $c_r$, and falls to its end point, which is at the predefined end time t3, with a predefined decay coefficient $c_d$. It has been found that such cortisol time response 26 (or response curve) can be estimated or modeled using the equation:

$$\text{Cortisol}(t) = g * \frac{\exp\left(-\frac{t}{c_d}\right)}{1 + \frac{c_r^2}{t^2}}, \quad (1)$$

where g is a gain, $c_r$ is the rise coefficient and $c_d$ is the decay coefficient. In particular, time t can be measured in minutes. The gain g corresponds to the height of the peak point P. Thus, the cortisol time response curve 26 can be modeled with a function with three key descriptors: gain g, rise coefficient $c_r$ and decay coefficient $c_d$. In this way an estimation of the cortisol response, which closely resembles a salivary cortisol response of the user in reality, can be provided. The stimulus response (or stress response) and the corresponding cortisol response clearly differs between males and females. Thus, the estimated cortisol response 26 can depend on an input information which is input into the system 100, for example input to the processing unit 10, and which indicates the sex of the user. The information can for example be input by means of a user interface, or it can be hard-coded in the system. By taking the sex of the user into account a more accurate estimation or determination of the level of mental balance (or imbalance) can be given. For example, the predefined end point of time t3 depends on the sex of the user. In particular, the predefined end point of time t3 can be about 90 minutes after the specific start point of time t1 if the input information indicates a female, and about 150 minutes if the input information indicates a male. Since the down curve is an asymptote, these values are chosen such that the cortisol response has effectively died out (but not exactly). Thus, at the end point of time t3 the cortisol level of the cortisol time response is zero or comes close to zero.

Table I below shows the modeling results for the three salivary cortisol response coefficients to a psychosocial stimulus (or stressor) for males and females according to equation (1) above. As can be seen in Table I, the rise coefficient $c_r$ is equal for both sexes, whereas the decay coefficient $c_d$ differs significantly. The gain g is almost twice as high for women compared to men.

TABLE I

| Coefficient | Male | Female |
|---|---|---|
| $c_d$ | 23 | 15 |
| $c_r$ | 28 | 28 |
| g | 155 | 270 |

The estimated cortisol time responses (cortisol levels over time) can be additional to a cortisol base level of a real cortisol trace. In a day trace of the cortisol there always is a base level dependant on the time of day. For example, in the morning it is high to wake a person up, and it lowers down to a low value in the evening to facilitate sleep. These effects of the cortisol base level should not be taken into account by the system. The cortisol time response (curve) disclosed herein is a cortisol level amount additional to the cortisol base level. This additional amount is vanished after a specific time period (e.g. about 150 minutes. Thus, cortisol level of the estimated cortisol time response is not an estimated value of a real (absolute value) cortisol level.

The cumulated (salivary) cortisol responses which overlap in time yield the estimated cortisol level trace. Since the estimated cortisol level trace is coupled to the stimuli (or stress/arousal peaks) in the skin conductance trace, the temporal effects of the occurrence of a stimulus (or stressor) in the skin conductance trace becomes visible in the estimated cortisol level trace. Subsequent stimuli (or stressors) clearly cause overlapping cortisol responses.

Thus, the estimated cortisol level trace 28 can be determined by cumulating multiple estimated cortisol time responses 26, wherein each estimated cortisol time response 26 is based on one stimulus response 24. In this way a quantification of the cumulative effect of subsequent stimuli (or stressors) in a specific time frame (e.g. a time frame of several hours) can be provided. Based on these cumulated cortisol responses the level of mental balance (or imbalance) can be estimated.

Figure 6:
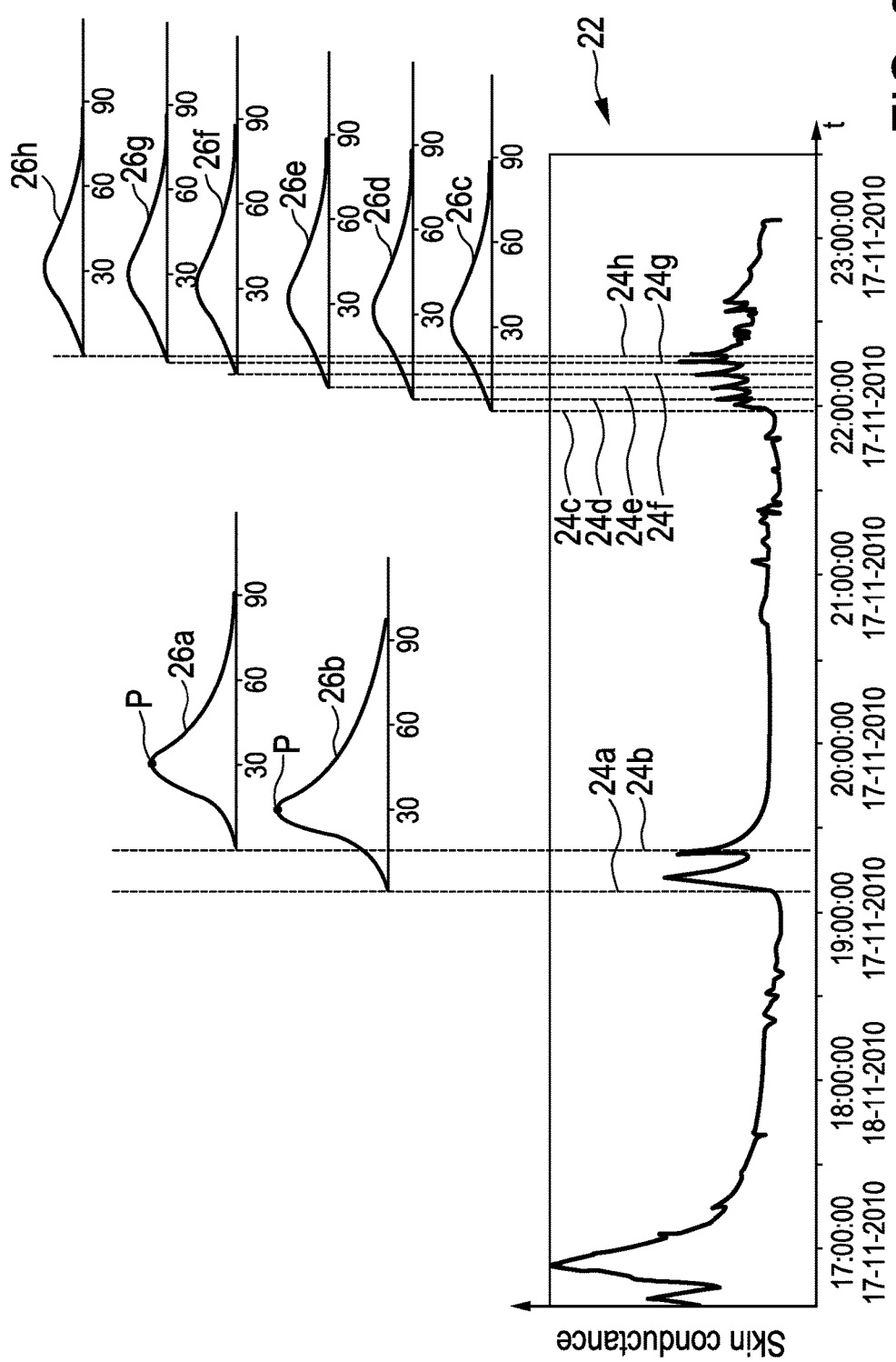
FIG. 6 shows an exemplary skin conductance trace having multiple stimuli and the corresponding cortisol time responses.

FIG. 6 shows an exemplary skin conductance trace 22 having multiple stimuli 24*a-h* and the corresponding cortisol time responses 26*a-h*. In particular FIG. 6 shows the skin conductance trace 22 of a female. The skin conductance trace 22 has multiple stimuli 24*a-h* (or stress/arousal peaks). Coupled to each stimulus response 24*a-h* is a corresponding or respective salivary cortisol response curve 26*a-h*. As can be seen in FIG. 6, the predefined peak point of time (t2 in FIG. 5) of the peak point P is about 30 minutes after the start point of time.

The estimated cortisol level trace 28 is then determined by cumulating the multiple estimated cortisol time responses which overlap in time (for example on the one hand cortisol responses 26*a* and 26*b* in FIG. 6, and on the other hand cortisol responses 26*c-h*). The mental balance is therefore determined or estimated based on the cumulative effect of subsequent stimuli (or stressors) on the mood/stress state of a person by assuming that it is related to the cumulative salivary cortisol, which is linked to the intracellular cortisol.

Figure 7:
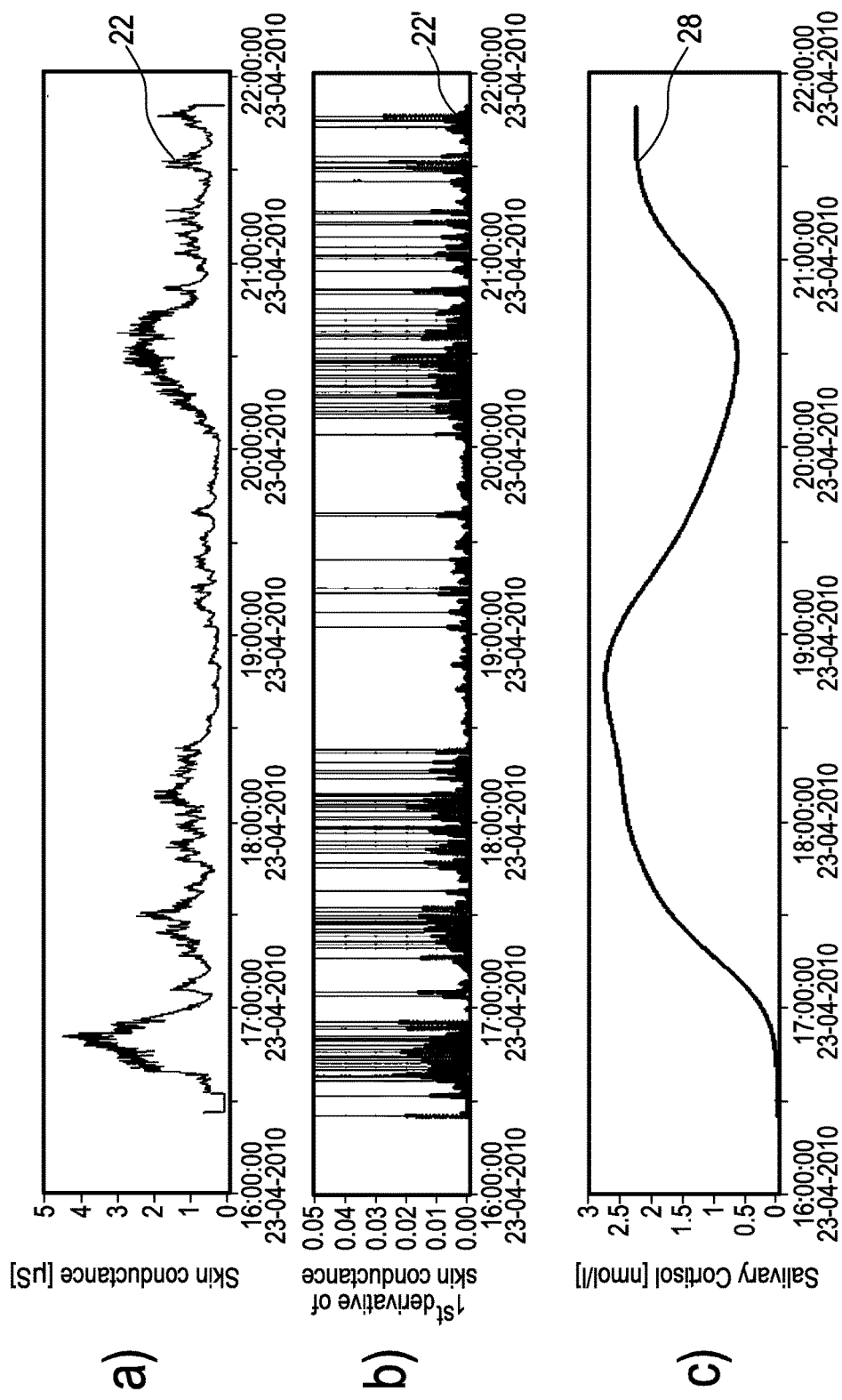
FIG. 7 shows a first example of a) a skin conductance trace, b) the first derivative of the skin conductance trace, and c) an estimated salivary cortisol level trace.
Figure 8:
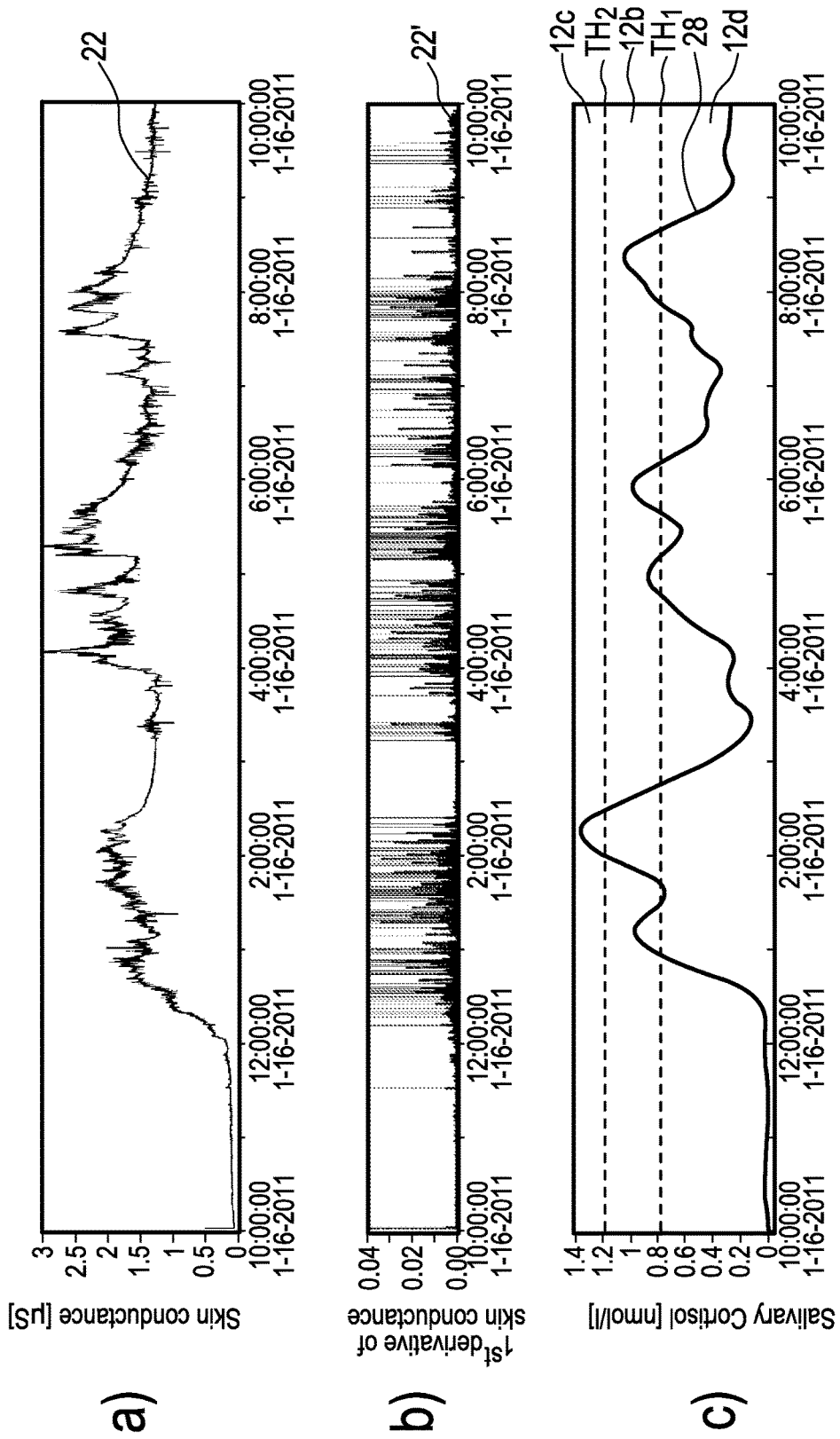
FIG. 8 shows a second example of a) a skin conductance trace, b) the first derivative of the skin conductance trace, and c) an estimated salivary cortisol level trace.

FIG. 7 shows a first example of a skin conductance trace 22 (FIG. 7*a*)), the first derivative 22' of the skin conductance trace (FIG. 7*b*)), and an estimated salivary cortisol level trace 28 (FIG. 7*c*)). FIG. 8 shows a second example of a skin conductance trace 22 (FIG. 8*a*)), the first derivative 22' of the skin conductance trace (FIG. 8*b*)), and an estimated salivary cortisol level trace 28 (FIG. 8*c*)). In particular, FIG. 7*a* or FIG. 8*a* shows the smoothed skin conductance, FIG. 7*b* or FIG. 8*b* shows the first derivative d(SC)/dt of the skin conductance and the corresponding peaks (indicated as fine vertical lines), and FIG. 7*c* or FIG. 8*c* shows the cumulative cortisol. Basically, each of FIG. 7 and FIG. 8 shows the signal processing performed by the processing unit 10 which leads to the determination of the estimated level of mental balance/imbalance (or cumulative stress load) based on the skin conductance trace or signal 22.

As explained above, the skin conductance sensor 20 measures the skin conductance (e.g. at a rate of 2 Hz). A skin conductance trace 22 is then formed (see FIG. 7*a*) or FIG. 8*a*)). The processing unit 10 then determines the first order derivative 22' of the skin conductance in order to determine the stimulus response(s) (see FIG. 7*b*) or FIG. 8*b*)). The processing unit 10 can determine the at least one stimulus response in the skin conductance trace by determining peaks in the first order derivative of the skin conductance. Thus, each stimulus response shows as a peak in the first derivative of the skin conductance (indicated by fine vertical line in FIG. 7*b* or FIG. 8*b*). The processing unit 10 then estimates or determines an estimated cortisol level trace 28 by cumulating multiple estimated cortisol time responses 26, each estimated cortisol time response 26 being based on one stimulus response 24 (see FIG. 7c) or FIG. 8c)). The processing unit 10 then determines the estimated level of mental balance based on the estimated cortisol level trace 28.

As mentioned above, emotional events give rise to peaks in the skin conductance trace 22 or signal. The rising edges of these peaks show as peaks in the first derivative. The severity of such stimulus (or emotional event), and hence the level of mental balance or allo static load of such events, is quantified by the height of the peak in the first derivative of the skin conductance trace or signal. The contribution of these stimulus/stimuli (or emotional event(s)) to the (salivary) cortisol level is then determined by adding a cortisol response curve 26 (such as shown in FIG. 1 or the bottom diagram of FIG. 6) to a memory or bookkeeping register (e.g. going 90 minutes into the future for females and 150 minutes into the future for males). The height of the cortisol response or cortisol contribution of an event (controlled by the gain constant g) is proportional to the height of the peak in the first derivative of the skin conductance trace 22 for that stimulus response. In this way the effect of an emotionally arousing event lingers on in the salivary (and hence the intracellular) cortisol concentration for a specific period of time, in particular 90 and 150 minutes for females and males respectively. In order to assess a current mental balance status, the past events need to be taken into account for these periods. Thus a measure of mental balance is estimated as the accumulated salivary cortisol through calculating the convolution of the height-adjusted (delta) peaks for a series of events on the on hand, and the male of female salivary cortisol response as parameterized in formula I on the other hand.

In the absence of stressors the cortisol level drops to the background level according to the cortisol time response curve in a specific period of time, in particular about 90 minutes for females and about 150 minutes for males. A fully balanced state is then defined as the state more than 90 or 150 minutes after the last significant stimulus or stimulus response for females and males respectively. A fully unbalanced state is harder to define. Clearly when a never ending sequence of stimuli (or stressors) only minutes apart occurs a steady state is obtained with a cortisol level linked to the (cumulative) severity of the perceived stressors. According to the allostatic (over)load literature at some point the stress response dies out in such a situation, when allostatic overload is reached. Albeit hard to define quantitatively, this state can be assigned the denomination "fully unbalanced". It is in this state that a person is prone to erratic behavior. For practical implementations, it is always possible to make the definition of "fully unbalanced" adaptive to the measured history of a particular user: the highest cortisol level calculated from the skin conductance measurements.

Compared to FIG. 7c), in FIG. 8 c) additionally three regions in the cumulative cortisol level or cortisol level trace 28 are indicated which are translated into to three corresponding intervals or regions 12a, 12b, 12c of mental balance (or imbalance). In a first region 12a the cumulative cortisol level is below a first threshold TH1, in a second region 12b the cumulative cortisol level is above the first threshold TH1 and below a second threshold TH2 (which is bigger than the first threshold TH1), and in a third region 12c the cumulative cortisol level is above the second threshold TH2. Each region 12a, 12b, 12c depicts or corresponds to one level or state of mental balance (or imbalance). The first region 12a can for example indicate a "safe balanced" or "green" level or state, the second region 12b can be indicate "call for attention" or "yellow" level or state, and the third region 12c can indicate a "take action" or "red" level or state. Therefore, FIG. 8 c) basically shows a translation of the salivary cortisol level into a "traffic light" color code.

An exemplary, but not limiting, "traffic light" interpretation of the allostatic load can be as follows. In the "green" state the person is relaxed and at ease. At a certain level of cortisol (which can be determined in trials by means of mood questionnaires, such as the UMACL), a transition from the "green" state to the "yellow" state is defined. In the "yellow" level or state the person is alert for possible dangers, and somewhat stressed. The response to stressors in the "yellow" state is bound to be different from that of a person in the "green" state. In the "red" state the person is in allostatic overload, and the cumulative effect of stressful events is considered harmful to the person. If a person stays in the "yellow" state for too long the cumulative allostatic load leads to the phenomenon of adrenal fatigue, which is accompanied with a lowered cortisol response curve to emotional events. Since cortisol functions as a moderating buffer for the activation of the person in terms of alertness a person stays into the alert and exited state for a longer time, and with higher intensity. A person is "edgy" in this state. The proportion of durations of green and yellow states is a measure for balance in this case. Too long presence in the yellow state wears the HPA axis out and leads to a red state. Possibly out of the statistics of the stress response the diminished response due to adrenal fatigue can be observed.

If one observes the cortisol curve in FIG. 8 closely a latency can be observed. The cortisol level trace 28 peaks about a half hour (30 minutes) after the stressor. This is true for each emotional event or stressor, but the effect is more visible with the strong emotional events or stressors. This latency allows a predictive capability of the system (or wearable device), to warn the user (e.g. wearer of the wearable device) of an upcoming peak. During such a maximum the response to new stressors differs from the 'normal' stress response. The response is bound to be more unbalanced, possibly even leading to bouts of anger, or road-rage, when driving a car. In the example of FIG. 8 insufficient recuperation was allowed after a sequence of stressors, leading to a period in the "red" state 12c. A totally stimulus free (or stimulus response free) period of about an hour restored the balance almost completely.

Up to this point the output in form of a "traffic light" color code or indication has been described. However, it will be understood that the feedback or output of the level or state of mental balance to the user can also be given in any other suitable way. In a preferred embodiment however, three (or more) different states are identified that depict various levels of mental balance. Instead of "green", "yellow" and "red", also other codes or symbols could be used, such as "relaxed", "busy" and "overloaded", or ":-)", ":-|" and ":-(".

Figure 9:
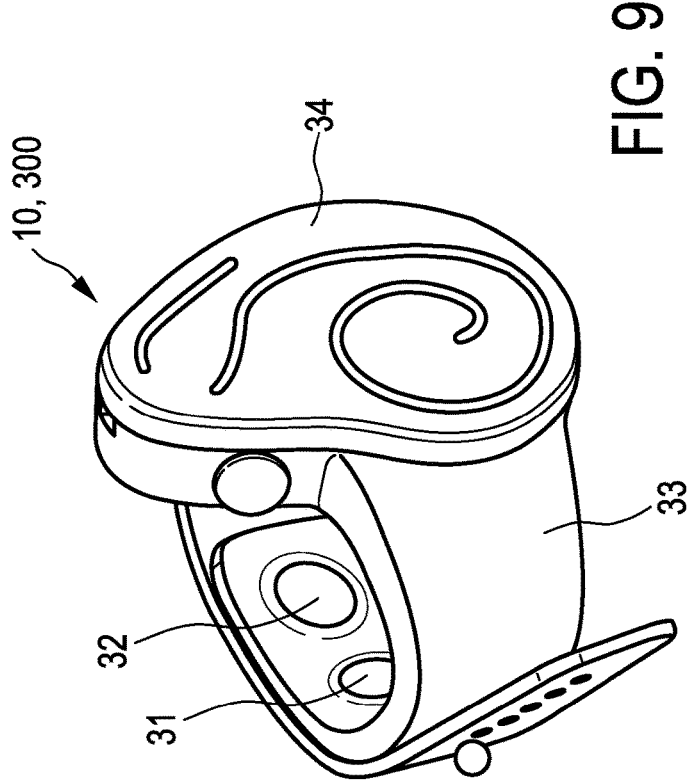
FIG. 9 shows a perspective view of a wearable device according to an embodiment.

FIG. 9 shows a perspective view of a wearable device 30 wearable by a user according to an embodiment. In this embodiment the wearable device 30 is in the form of a wristband. The wristband comprises a wristband material part 33 and a casing 34. The wristband material part 33 can loop around the wrist of the user. It will be understood that the wearable device 30 could also be worn around any other suitable body part, such as the ankle, foot or hand.

The wearable device 30 can in particular comprise the mental balance or imbalance estimation system 100 described herein. In this way a mental balance or imbalance estimation system 100 in an unobtrusive and wearable format can be provided. Alternatively, the wearable device 30 can only comprise the skin conductance sensor 20 and the processing unit 10 of the system 100 can be located at a remote location or device (e.g. a remote computer).

The wearable device 30 comprises the skin conductance sensor 20. The skin conductance sensor 20 comprises skin conductance electrodes 31, 32 in combination with a skin conductance measuring unit (not shown). In the embodiment of FIG. 9, two skin conductance electrodes 31, 32 are integrated into the wrist band material part 33. The skin conductance electrodes 31, 32 can be arranged so as to contact the volar side of the wrist, where there is normally not a lot of hair, when the wearable device 30 is put on or worn by the user. In this way, a better measurement of the skin conductance can be provided.

The skin conductance measuring unit is adapted to measure the skin conductance of the user 1 between the skin conductance electrodes 31, 32. The skin conductance electrodes 31, 32 can be connected to the skin conductance measuring unit by means of wires integrated in the wristband material part 33 in the embodiment of FIG. 9. In particular, the skin conductance measuring unit or sensor can comprise a voltage generator for applying a voltage between the at least two skin conductance electrodes, a sensing unit for sensing a current between the at least two electrodes, and/or a calculating unit for calculating the skin conductance based on the sensed current. The measured skin conductance over time forms the skin conductance trace (or data). The skin conductance trace (or data) can for example be stored in a memory of the wearable device 30, or can be (wirelessly) transmitted to an external unit using a (wireless) transmitter.

The skin conductance measuring unit and/or the processing unit 10 can be integrated into the casing 34 of the wearable device 30. The wearable device 30 can further comprise a transmitter for wirelessly transmitting data over a wireless communication link, such as the output data or the estimated level 12. However, it will be understood that the processing unit 10 can also be a separate part or device and that the wearable device 10 then transmits the skin conductance data to the separate part or device via the (wireless) transmitter.

Figure 10:
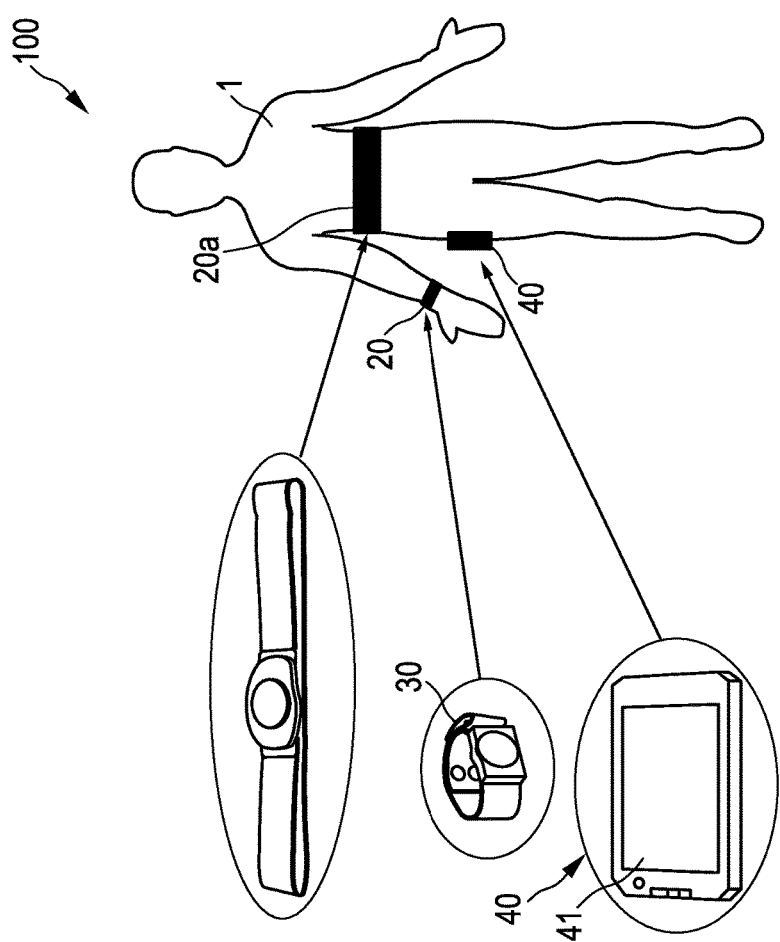
FIG. 10 shows a user and a mental balance or imbalance estimation system according to an embodiment, FIG. 11a-11d each shows an output unit of a mental balance or imbalance estimation system according to an embodiment.
Figure 11A:
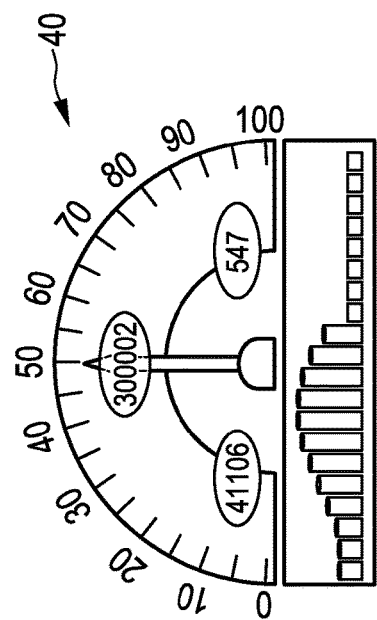
Figure 11B:
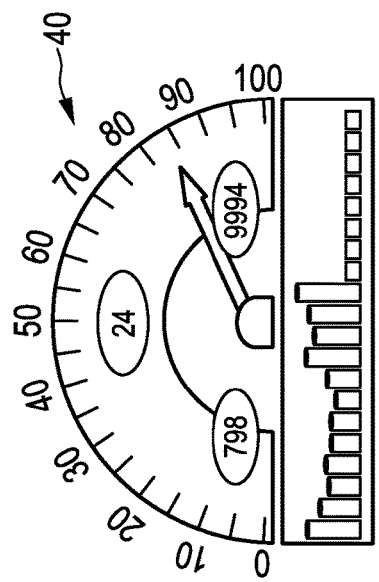
Figure 11C:
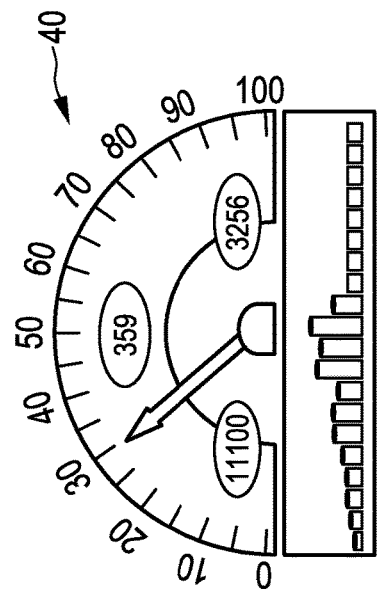
Figure 11D:
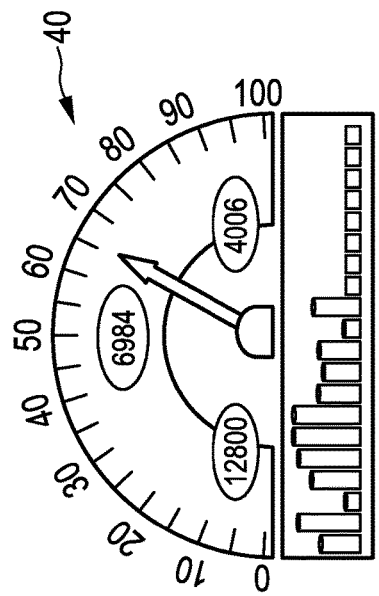

FIG. 10 shows a user 1 and a mental balance or imbalance estimation system 100 according to an embodiment. The mental balance or imbalance estimation system 100 comprises a skin conductance sensor 20 for sensing the skin conductance of the user 1. In FIG. 10, the skin conductance sensor 20 is integrated into a wearable device 30, in form of a wristband, wearable by the user 1. However, the skin conductance sensor 20 can also sense the skin conductance at other suitable body parts, such as the finger(s), and/or at the palmar or volar side of the hand. The mental balance or imbalance estimation system 100 further comprises an output device 40 for outputting the level 12 of mental balance or imbalance to the user 1. The output device 40 can be portable, for example be clipped to a belt of the user 1 as indicated in FIG. 10. The output device 40 shown in FIG. 5 comprises display means 41 for displaying the level 12 of mental balance or imbalance. Alternatively or additionally, the level 12 can also be output to the user 1 using sound, light, and/or vibration. The output device 40 can be a separate device (as shown in FIG. 10), or it can be integrated into for example the wearable device 30 comprising the sensor 20. The output can be through a variety of modalities such as audio (e.g. sound), visual (e.g. light), and/or haptic (e.g. vibration) feedback.

The mental balance or imbalance estimation system 100 can further comprise additional devices, such as an electrocardiogram (ECG) sensor, like the ECG chest belt 20a shown in FIG. 10. The ECG sensor can sense the electrocardiogram of the user 1. From the electrocardiogram the heart rate variability (HRV) can be determined, which is known to relate to stress. However, also other suitable measurements such as BVP, respiration, skin temperature, electroencephalography (EEG)/brain activity, activity measurement (e.g. through an accelerometer) and/or questionnaires can be used for additional measurements.

FIG. 11a-11d each shows an output unit 40 of a mental balance or imbalance estimation system 100 according to an embodiment. In this example the output unit 40 is or comprises a display, as explained with reference to FIG. 10. In each of FIG. 11a-d the information about the state or level of mental balance (or imbalance) is communicated by means of a colored speedometer. For example, the display of FIG. 11a can be green, indicating a "green" level or state, the display of FIG. 11b can be yellow, indicating a "yellow" level or state, the display of FIG. 11c can be red, indicating a "red" level or state, and the display of FIG. 11d can be blue, indicating a "blue" level or state. Therefore, in this example, four different states are identified that depict various levels of mental balance.

In one example, this "traffic light" advisor can be used to warn the wearer of the wearable device 30 (or wristband) described herein about an "out of balance" period in the near future (e.g. the next 60 minutes). Thus, the wearable device 30 (or wristband or wristband GSR sensor) is used for monitoring of level of mental balance/imbalance (or stress level) and predicting or forecasting a cumulative stress response within a specific timeframe (e.g. 60 minutes) in order to warn the user of the upcoming potentially harmful or strong (emotional) imbalance, or high level of mental imbalance. The upcoming level of mental imbalance is displayed to the user as a color coded bar, or a dashboard (as shown in FIG. 11a-d), so that the user would see on the wristband display the moment he approaches the "red" state or zone. If approaching the "red" zone is forecasted by the system or wearable device (e.g. wristband), the user can for example be notified by a vibration or an auditory signal. The system or wearable device (e.g. wristband) can be coupled with an external device (e.g. an iPhone or an PC application) that can provide behavioral tips to counter the predicted stress peak (e.g. breathing exercises), advice to avoid stressful situations, advice to control one's temper if in stressful situation, take a walk in a park, etc. The external device (e.g. iPhone or PC) could also start displaying nature images or classical music that are known to reduce stress.

Figure 12:
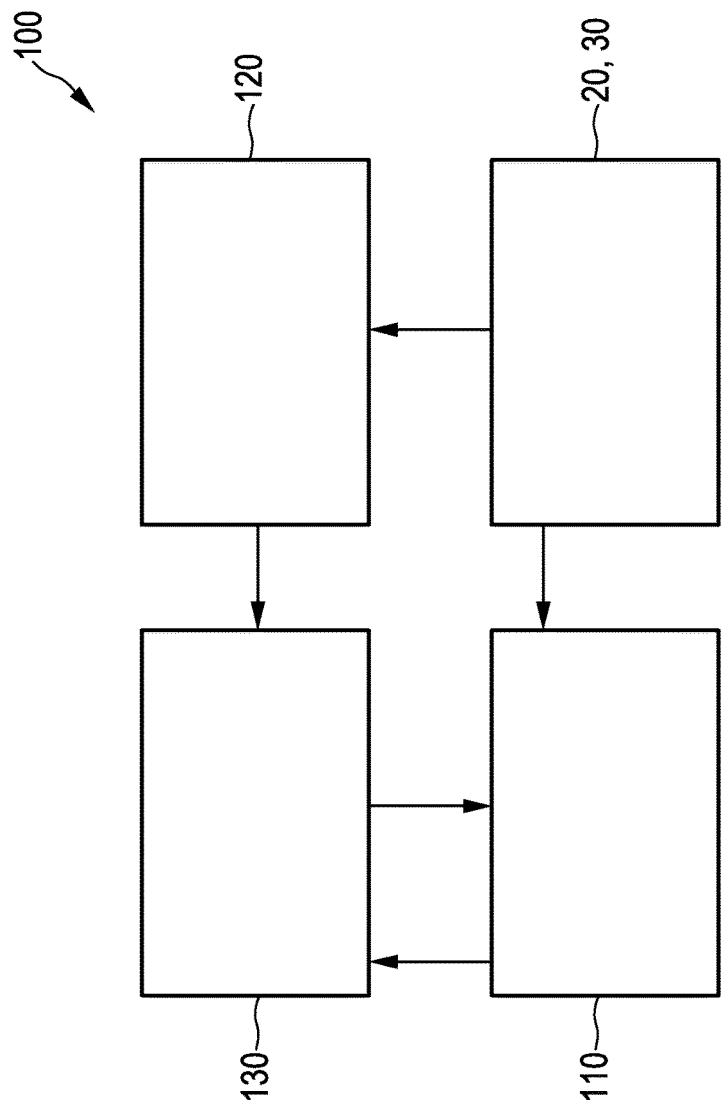
FIG. 12 shows a diagram of a mental balance or imbalance estimation system or method according to an embodiment.

FIG. 12 shows a diagram of a mental balance or imbalance estimation system 100 or method according to an embodiment. The system 100 comprises a skin conductance sensor 20, in particular a wearable device 30 (or a wristband GSR sensor), a mental imbalance level estimator 110 based on past emotional events (or stimuli), a mental imbalance level predictor (or forecaster) 120 for a future time or time period (e.g. for the upcoming 60 minutes), and a calendar application 130 (or electronic agenda). As can be seen in FIG. 12, the skin conductance sensor 20 or wearable device 30 (or wristband GSR sensor) transmits the skin conductance trace to the mental imbalance level estimator 110 based on past emotional events (or stimuli). The mental imbalance level estimator 110 determines the estimated mental imbalance level for the current point of time, as explained above. This estimated mental imbalance level is then associated with or related to data from the calendar application 130 of the user. This calendar application 130 can for example be implemented in an external device (e.g. PC, laptop, mobile phone, iPhone, etc.). Alternatively or cumulatively, the skin conductance sensor 20 or wearable device 30 (or wristband GSR sensor) transmits the skin conductance trace to the mental imbalance level predictor (or forecaster) 120 for a future time or time period (e.g. for the upcoming 60 minutes). The mental imbalance level predictor 120 determines the estimated mental imbalance level for a future point of time or future period of time, as explained above. This estimated mental imbalance level is then associated with or related to data from the calendar application 130 of the user. In this way, the level of mental imbalance can be predicted or forecasted for an upcoming event in the calendar of the user. This is in particular achieved by taking into account both the current level of mental imbalance and the predicted (forecasted) level of mental imbalance for a specific future time period (e.g. next 60 min).

It will be understood that the mental imbalance level estimator 110 and/or mental imbalance level predictor 120 can be implemented in the same processing unit or can be implemented in separate processing units. Further, it will be understood that the processing unit(s) of the mental imbalance level estimator 110 and/or mental imbalance level predictor 120 can be located in the wearable device 30 (in particular wristband GSR sensor) or can be located in an external device (e.g. PC, laptop, mobile phone, iPhone, etc.).

In this example illustrated in FIG. 12, the system 100 or wearable device 30 (e.g. wristband or wrist worn GSR sensor) described herein is used in combination with an application running on an external device (e.g. PC, laptop, mobile phone, iPhone, etc.) in order to estimate or monitor the level of mental imbalance, analyze this level of mental imbalance and relate it to data from an electronic agenda of the user in order to predict or forecast the level of mental imbalance for upcoming events by taking into account the user current level of mental imbalance and his predicted level of mental imbalance within a specific time period (e.g. 60 min timeframe). This system facilitates planning events in the agenda to avoid too high level of mental imbalance and provides the user with behavioral guidance to cope in cases of elevated level of mental imbalance.

A lightweight and unobtrusive wearable device is described herein that measures the occurrence and intensity of a person's emotional load (irrespective of valence, thus the emotions can be both positive and negative—both will constitute an emotional load), also called level of mental balance (or imbalance), and processes this data to deliver an output (e.g. a traffic light advisor) for the user (or wearer) of the device to signal a current status, and/or to warn for an out of balance period (e.g. during the next 60 minutes).

A system is described herein to derive a measure for mental balance derived from skin conductance measurements, in particular done with a wearable device. This measure can not only give an indication of the momentary state of mental balance of a person, but it can also make an estimation of the upcoming levels of mental balance. As such it can guide a person to prevent over-stressed states that can be harmful to a person's health. Moreover, it could use the forecast of upcoming mental balance in relation to other known upcoming events (e.g. from an agenda) in order to predict situations that are potentially harmful to a person's health.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device wearable by a user, the device comprising:
a band to be wrapped around an appendage of a user;
a casing coupled to the band, wherein the casing includes a display on a first side and a skin conductance sensor on a second, opposite side;
a sensor system comprising:
the skin conductance sensor positioned on the casing configured for sensing a skin conductance of the user; and
an estimation system comprising:
a processing unit operatively coupled to the display and configured to:
receive from the skin conductance sensor information regarding the skin conductance of the user;
determine one or more skin conductance traces based on the information regarding skin conductance of the user received over a known period of time;
determine a plurality of stimulated responses in the one or more skin conductance traces;
determine a plurality of estimated cortisol-level traces of the user based on the plurality of stimulated responses, wherein each respective estimated cortisol-level trace of the plurality of estimated cortisol-level traces extends an amount of time after a respective stimulated response of the plurality of stimulated responses;
determine a quantification of a cumulative stress load of the user based on the plurality of estimated cortisol-level traces, wherein the quantification of the cumulative stress load is determined based on the plurality of estimated cortisol-level traces with respect to at least one threshold value; and
output to the display information indicative of the quantification of the cumulative stress load in a form of a presentable level selected from a plurality of presentable mental imbalance levels.

2. The device of claim 1, wherein each of the plurality of stimulated responses is determined as a first order derivate of a corresponding skin conductance trace.

3. The device of claim 1, comprising:
a transmitter transmitting the quantification of the cumulative stress load to a remote terminal.

4. The device of claim 1, wherein the quantification of the cumulative stress load is determined based on the plurality of estimated cortisol-level traces exceeding the at least one threshold level among a plurality of threshold levels.

5. The device of claim 1, wherein the estimation unit receives secondary sensor information from at least one remote secondary sensor.

6. The device of claim 1, wherein the information indicative of the quantification of the cumulative stress load includes at least three different states, wherein each of the at least three different states is a level of the quantified cumulative stress load.

7. The device of claim 6, wherein the at least three different states includes a colored speedometer with a first section in a first color that represents the first state, a second section in a second color that represents the second state, and a third section in a third color that represents the third state, wherein the first, second, and third colors are visually distinct from each other.

8. A system for quantifying a cumulative stress load, the system comprising:
 a wearable device comprising:
  a band to be wrapped around an appendage of a user, wherein a skin conductance sensor is integrated into the band;
  a sensor system comprising:
   the skin conductance sensor positioned on the band configured for sensing a skin conductance of the user; and
   a wireless transmitter configured to provide information regarding the skin conductance of the user; and
 an external device comprising:
  a display; and
  a processing unit configured to:
   wirelessly receive from the wireless transmitter the information regarding the skin conductance of the user;
   determine one or more skin conductance traces based on the information regarding the skin conductance of the user received over a known period of time;
   determine a plurality of stimulated responses in the one or more skin conductance traces;
   determine a plurality of estimated cortisol-level traces of the user based on the plurality of stimulated responses, wherein each respective estimated cortisol-level trace of the plurality of estimated cortisol-level traces extends an amount of time after a respective stimulated response of the plurality of stimulated responses;
   cumulate a plurality of estimated cortisol-level traces; and
   determine a quantification of the cumulative stress load of the user based on the plurality of estimated cortisol-level traces, wherein the quantification of the cumulative stress load is determined based on the plurality of estimated cortisol-level traces with respect to at least one threshold value; and
   output to the display information indicative of the quantification of the cumulative stress load in a form of a presentable level selected from a plurality of presentable mental imbalance levels.

9. A device wearable by a user, the device comprising:
 a band to be wrapped around an appendage of a user;
 a casing coupled to the band, wherein the casing includes a display;
 a skin conductance sensor positioned on an interior surface of the band separate from the casing, wherein the skin conductance sensor is configured for sensing a skin conductance of the user; and
 an estimation system comprising:
 a processing unit operatively coupled to the display and configured to:
  receive from the skin conductance sensor information regarding the skin conductance of the user;
  determine one or more skin conductance traces based on the information regarding the skin conductance of the user received over a known period of time;
  determine a plurality of stimulated responses in the one or more skin conductance traces;
  determine a plurality of estimated cortisol-level traces of the user based on the plurality of stimulated responses, wherein each respective estimated cortisol-level trace of the plurality of estimated cortisol-level traces extends an amount of time after a respective stimulated response of the plurality of stimulated responses;
  determine a quantification of a cumulative stress load of the user based on the plurality of estimated cortisol-level traces, wherein the quantification of the cumulative stress load is determined based on the plurality of estimated cortisol-level traces with respect to at least one threshold value; and
  output to the display information indicative of the quantification of the cumulative stress load in a form of a presentable level selected from a plurality of presentable mental imbalance levels.

* * * * *